United States Patent
Domkowski et al.

(10) Patent No.: US 8,034,041 B2
(45) Date of Patent: Oct. 11, 2011

(54) PORT CLOSURE SYSTEM FOR INTRAVENOUS FLUID CONTAINER

(75) Inventors: John Domkowski, Kenosha, WI (US); Richard F. Daubert, Jr., Arlington Heights, IL (US)

(73) Assignee: Hospira, Inc., Lake Forest, IL (US)

( * ) Notice: Subject to any disclaimer, the term of this patent is extended or adjusted under 35 U.S.C. 154(b) by 156 days.

(21) Appl. No.: 12/410,911

(22) Filed: Mar. 25, 2009

(65) Prior Publication Data

US 2009/0192484 A1    Jul. 30, 2009

Related U.S. Application Data (63) Continuation of application No. 11/315,840, filed on Dec. 21, 2005, now Pat. No. 7,530,974, which is a continuation-in-part of application No. 11/023,889, filed on Dec. 23, 2004, now Pat. No. 7,488,311.

(51) Int. Cl.
  *A61B 19/00* (2006.01)
(52) U.S. Cl. .......... 604/415; 604/403; 604/410
(58) Field of Classification Search .......... 604/403, 604/408, 411, 415, 256; 220/62.22; 206/363–366; 383/210.1
See application file for complete search history.

(56) References Cited

U.S. PATENT DOCUMENTS

| | | |
|---|---|---|
| 3,205,889 A | 9/1965 | Alder et al. |
| 3,364,930 A | 1/1968 | Ryan |
| 3,547,401 A | 12/1970 | Beall et al. |
| 3,792,794 A | 2/1974 | Cutter et al. |
| 3,904,059 A | 9/1975 | Bellamy et al. |
| 4,158,362 A | 6/1979 | Durrett et al. |
| 4,412,573 A | 11/1983 | Zdeb |
| 4,478,342 A | 10/1984 | Slater et al. |
| 4,484,916 A | 11/1984 | McPhee |
| 4,523,691 A | 6/1985 | Larkin et al. |
| 4,528,220 A | 7/1985 | Hwo |
| 4,592,092 A | 5/1986 | McPhee |

(Continued)

FOREIGN PATENT DOCUMENTS

EP        0766955 B1    11/2000

(Continued)

OTHER PUBLICATIONS

Inoue, Fujio, "A New Package For A Kit Product: A Multiple Chamber Plastic Bag Packaging Parenteral Powder Drug and Diluent", PDA Asian Symposium & Exhibit, Tokyo ' 94.

(Continued)

*Primary Examiner* — Leslie R Deak
(74) *Attorney, Agent, or Firm* — Michael R. Crabb (57) ABSTRACT

A port closure system for use with a fluid container having fluid ports includes administrative and additive port closure assemblies. The administrative assembly receives a piercing pin and includes an administrative housing which seals closed one fluid port. A sleeve extends from an interior surface past a base surface in the administrative housing. The sleeve has an upper portion and a lower portion, of differing diameters. A cap assembly mates with the administrative housing, sealing the interior surface of the administrative housing. A removable cap provides access to the interior surface. The additive assembly receives a needle and includes a reseal housing which seals closed another fluid port. Another cap assembly mates with the reseal housing, sealing an interior face of the reseal housing. Another removable cap provides access to the interior face. A reseal element is mechanically retained between the reseal housing and cap assembly.

3 Claims, 9 Drawing Sheets

U.S. PATENT DOCUMENTS

| | | | |
|---|---|---|---|
| 4,694,971 | A | 9/1987 | Elsmo et al. |
| 4,724,028 | A | 2/1988 | Zabielski et al. |
| 4,757,911 | A | 7/1988 | Larkin et al. |
| 4,786,279 | A | 11/1988 | Wilkinson et al. |
| 4,892,222 | A | 1/1990 | Schmidt et al. |
| 4,898,584 | A | 2/1990 | Borsanyi et al. |
| 4,951,845 | A | 8/1990 | Pezzoli et al. |
| 5,088,995 | A | 2/1992 | Packard et al. |
| 5,314,084 | A | 5/1994 | Folta et al. |
| 5,334,180 | A | 8/1994 | Adolf et al. |
| 5,391,350 | A | 2/1995 | Wagner |
| 5,405,333 | A | 4/1995 | Richmond |
| 5,493,845 | A | 2/1996 | Adolf et al. |
| 5,498,253 | A | 3/1996 | Aswad et al. |
| 5,514,123 | A | 5/1996 | Adolf et al. |
| 5,632,396 | A * | 5/1997 | Burns ............... 215/247 |
| 5,738,663 | A | 4/1998 | Lopez |
| D402,366 | S | 12/1998 | Barney et al. |
| 5,924,584 | A | 7/1999 | Hellstrom et al. |
| 6,139,534 | A | 10/2000 | Niedospial, Jr. et al. |
| 6,162,206 | A | 12/2000 | Bindokas et al. |
| 6,179,821 | B1 | 1/2001 | Caspary et al. |
| 6,179,822 | B1 | 1/2001 | Niedospial, Jr. |
| 6,231,936 | B1 | 5/2001 | Kozimor et al. |
| 6,280,431 | B1 | 8/2001 | Domkowski et al. |
| 6,287,289 | B1 | 9/2001 | Niedospial, Jr. |
| 6,399,704 | B1 | 6/2002 | Laurin et al. |
| 6,468,377 | B1 | 10/2002 | Sperko et al. |
| 6,604,561 | B2 * | 8/2003 | Py ............... 141/329 |
| 6,723,076 | B1 | 4/2004 | Strobel |
| 7,488,311 | B2 | 2/2009 | Domkowski et al. |
| 7,726,498 | B2 * | 6/2010 | Anraku et al. ............. 215/247 |
| 7,828,787 | B2 | 11/2010 | Brandenburger et al. |

FOREIGN PATENT DOCUMENTS

| | | |
|---|---|---|
| JP | 55-166243 A | 11/1980 |
| JP | 63-135641 A | 9/1988 |
| JP | 2-58439 A | 4/1990 |
| JP | 626563 A | 4/1994 |
| JP | 2675049 B2 | 7/1997 |
| JP | 10-230009 A | 9/1998 |
| WO | 9640037 A1 | 12/1996 |
| WO | 02/072175 A1 | 9/2002 |

OTHER PUBLICATIONS

McGraw, Inc., Discussion Guide, (Duplex Focus Groups) Oct. 24, 1994 (3 pages).

Engineering Drawing No. S6272, entitled "Duplex Container, Oct. 1994".

B. Braun Medical Inc., Brochure, ©2003 B. Braun Medical Inc. Y07-530-307 (Sep. 2003).

B. Braun Medical Inc., website:www.bbraunusa.com, "IV Solutions" on Mar. 4, 2004.

* cited by examiner

PORT CLOSURE SYSTEM FOR INTRAVENOUS FLUID CONTAINER

CROSS-REFERENCE TO RELATED APPLICATION(S)

This application is a continuation of U.S. Ser. No. 11/315,840, which was filed Dec. 21, 2005, now U.S. Pat. No. 7,530,974, which is a continuation-in-part of U.S. Ser. No. 11/023,889, which is now U.S. Pat. No. 7,488,311 filed Dec. 23, 2004.

BACKGROUND OF THE INVENTION

The present invention relates to the field of containers for administering medical fluids to patients. More particularly, the present invention relates to a port closure system for intravenous (IV) fluid containers.

Access ports are commonly used in infusion solution containers to administer solutions to a patient, or to add medicaments or other solutions to the container prior to administration. Current solution containers typically may include a dedicated outlet port for solution administration to a patient and a dedicated inlet port for the addition of diluent or other ingredients to the container.

The outlet port is intended to be coupled to an administrative set and is therefore commonly referred to as the administrative port, whereas the inlet port is designed to permit the injection of therapeutic agents and nutrients into the partially filled container and is sometimes identified as the additive port. Such a container may contain a partial filling of a sterile solution such as saline or dextrose to function as a diluent for the injected additive. The diluted drug or nutrient is then administered to a patient by means of the administrative set that may be either directly or indirectly (i.e., through another solution set) coupled to the patient.

Maintaining the sterility of the fluid to be administered is of major importance. It has been found, however, that careless or inattentive handling of a solution container, as connections are made for fluid administration or additive introduction, may create significant risks of contamination. Such risks may be increased where emergency situations are presented that require quick manipulation of the various components.

Autoclave sterilization of the assembled container and ports is time and energy intensive. The innermost parts of the assembled ports, contact surfaces and any air voids therebetween that the steam cannot reach are more difficult to autoclave than the rest of the container. The temperature and/or the duration of the autoclave cycle must be increased for the difficult to reach areas to be properly sterilized.

Therefore, an object of this invention is to provide an additive port closure assembly to reduce the possibility of contamination during storage and use.

A further object of the invention is to provide an additive port closure assembly to improve the ease of handling when fluids are to be withdrawn or introduced.

Another object of the invention is to provide an additive port closure assembly to increase the ease and efficiency of manufacture.

A further object of the invention is to provide an administrative port closure assembly to reduce the possibility of contamination during storage and use.

A further object of the invention is to provide an administrative port closure assembly to improve the ease of handling when fluids are to be withdrawn or introduced.

A further object of the invention is to provide an administrative port closure assembly that is adaptable to receive administrative sets with spikes or pins of different diameters with consistent insertion and removal forces and without leakage.

Another object of the invention is to provide an administrative port closure assembly to increase the ease and efficiency of manufacture.

These and other objects will be apparent to those skilled in the art.

SUMMARY OF THE INVENTION

A port closure system for use with a fluid container having fluid ports may include administrative and additive port closure assemblies. The administrative port closure assembly receives a piercing pin and includes an administrative housing which seals closed one fluid port. A sleeve extends from an interior surface past a base surface in the administrative housing. The sleeve has an upper portion and a lower portion, of differing diameters. A cap assembly mates with the administrative housing, sealing the interior surface of the administrative housing. A removable cap provides access to the interior surface.

The additive port closure assembly receives a needle and includes a reseal housing which seals closed another fluid port. A cap assembly mates with the reseal housing, sealing an interior face of the reseal housing. As with the administrative port closure assembly, a removable cap provides access to the interior face. A reseal element is mechanically retained, secured or captured between the reseal housing and cap assembly.

DESCRIPTION OF THE DRAWINGS

FIG. 20 is similar to FIG. 19 but shows the same area after the cap assembly is joined to the reseal housing.

DETAILED DESCRIPTION OF THE EMBODIMENTS OF THE INVENTION

With reference to FIGS. 1-3A, a port closure system 10 is shown for use with a fluid container 12, which may have first and/or second fluid ports 14 and 16 accessible respectively with a syringe needle 18 and piercing pin set 20. Fill tubes 13, 15 define the fluid ports 14 and 16 respectively.

With reference to FIGS. 2-5, the port closure system 10 includes two port closure assemblies; with the first port assembly being an additive port closure assembly 22 adapted to provide needle 18 sterile access to the first fluid port 14. The additive port closure assembly 22 is adapted to be assembled and sterilized as a subassembly prior to association and use with the fluid container 12.

Figures 4, 5, 6A:
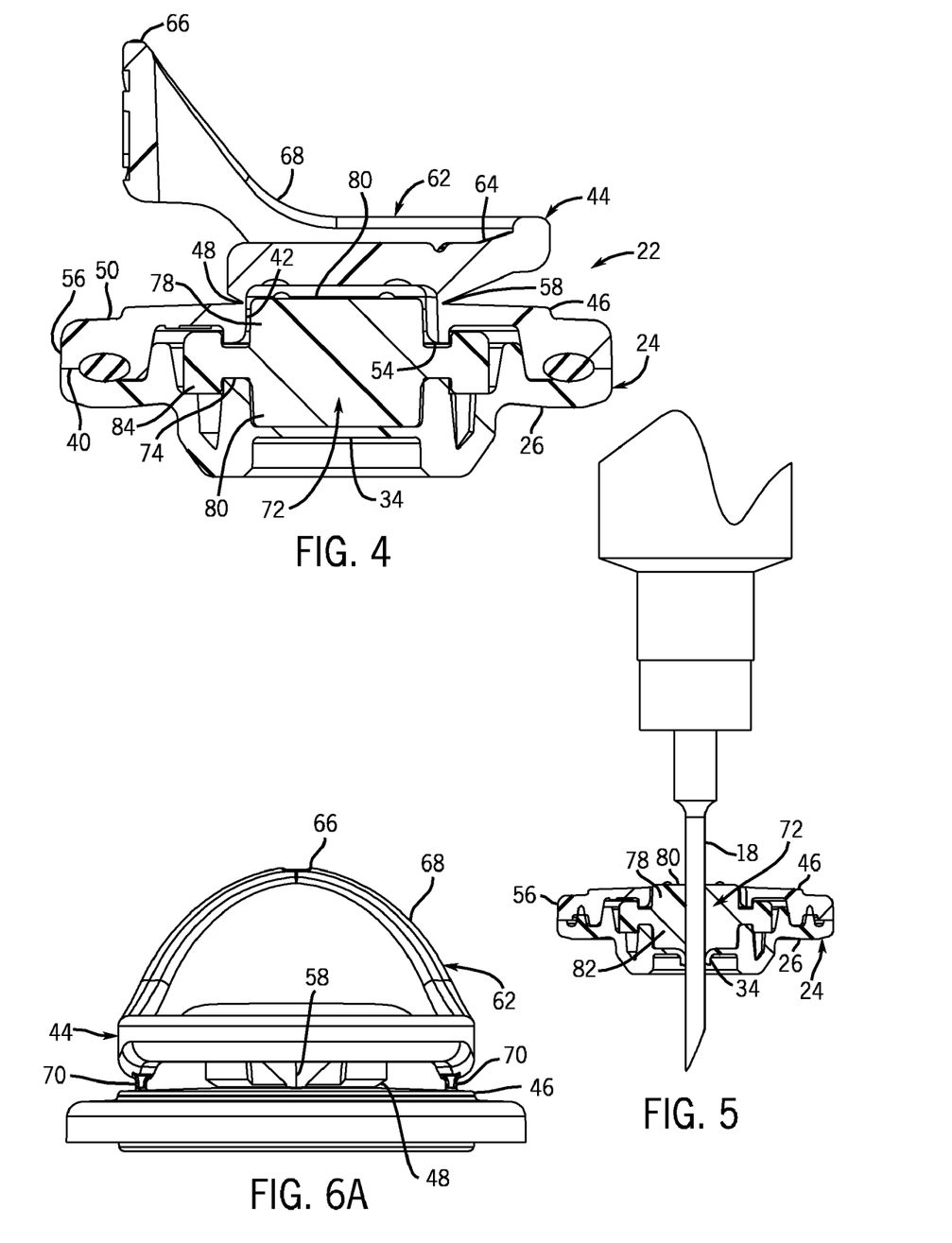
FIG. 4 is a sectional view of the additive port closure assembly of the present invention.
FIG. 5 is a sectional view of the additive port closure assembly of the present invention in use with a needle.
FIG. 6A is a side view of the cap assembly of the present invention.

The additive port closure assembly 22 includes a port housing 24 (hereinafter "reseal housing 24") adapted to seal closed the first fluid port 14 by attachment to the fill tube 13. The reseal housing 24 has a base face 26 adapted to be associated with the first fluid port 14 or fill tube 13 and an interior face 28 adapted to face outwardly from the first fluid port 14. An open cylinder 30 extends from the interior face 28 to the base face 26 and has an upper rim 32. A reseal diaphragm 34 is connected to the open cylinder 30 to seal the open cylinder 30 closed to fluid flow from the container 12. The reseal diaphragm 34 is opened to fluid flow once pierced by needle 18. A reseal flange 36 extends generally radially from the open cylinder 30. The reseal flange 36 protects the user from accidental pricks when applying needle 18 to the additive port closure assembly 22.

The reseal flange 36 and open cylinder 30 are also oriented and arranged to accommodate a commercially available needle-less access system (not shown) being integrated with the reseal housing 24. U.S. Pat. No. 5,924,584 describes one embodiment of a needle-less access system suitable for the present invention; said description is expressly incorporated herein in its entirety.

With reference to FIGS. 3A-6C, a cap assembly 38 of additive port closure assembly 22 is connected to the reseal housing 24. In general, the cap assembly 38 includes an under shell 40 shaped to mate with the interior face 28 of the reseal housing 24. Once mated, the cap assembly 38 seals the interior face 28 from potential contamination. A sealed opening 42 is provided in cap assembly 38, and a removable cap 44 provides access to the sealed opening 42 and the interior face 28. Once the removable cap 44 is detached, the additive port closure assembly 22 need not be re-sterilized, as the cap assembly 38 operates as a sterile barrier to shield the interior face 28 from potential contamination. Removable cap 44 is tamper evident as it cannot be reconnected once removed. Furthermore, if the cap 44 is pierced while still in place, it clearly shows that a hole has been made in the cap (i.e., tampering has taken place).

Figure 6B:
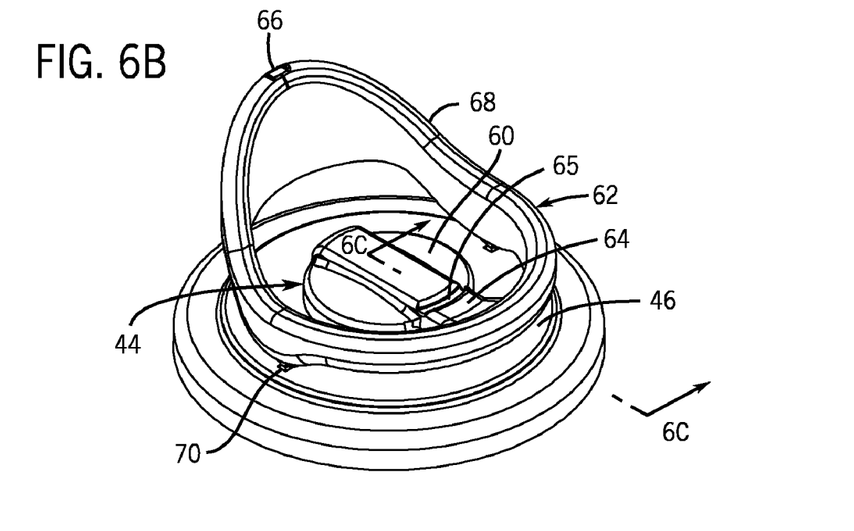
FIG. 6B is a perspective view of the cap assembly of the present invention.

The cap assembly 38 is of unitary construction and includes a crown 46 connected to the removable cap 44 by an annular frangible area 48. The term "frangible area" as used herein refers to any breakable area or any area with some form of breakable seal.

The crown 46 of the cap assembly 38 has an outer shell 50. The sealed opening 42 extends between the outer and under shells 50 and 40 and provides access to the interior face 28 when the removable cap 44 is detached. A retaining rim 54 extends from the under shell 40 and around the sealed opening 42. A crown flange 56 extends generally radially from the sealed opening 42. The crown flange 56 protects the user from accidental pricks when applying needle 18 to the additive port closure assembly 22.

Figure 6C:
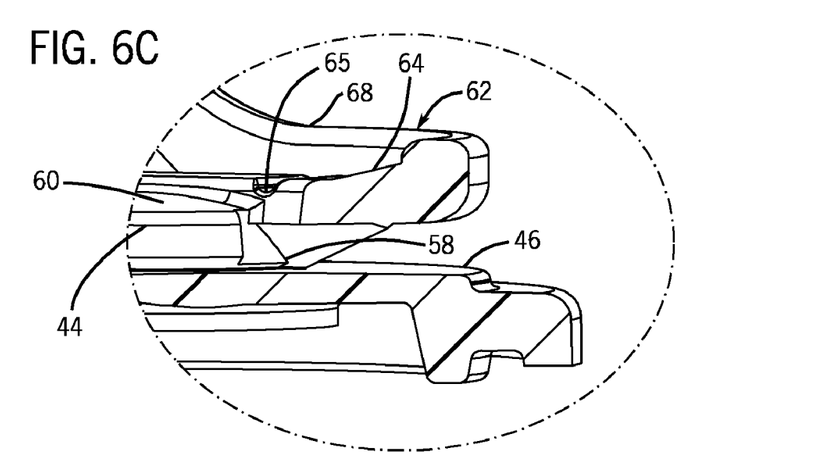
FIG. 6C is an enlarged partial sectional view of the notched portion of the cap assembly taken along line 6C-6C in FIG. 6B.

A notch area 58 is formed on the cap assembly 38 and is operatively associated with the frangible area 48 to weaken the frangible area 48 near the notch area 58. One skilled in the art will appreciate that the notch area 58 can be on the removable cap 44, as shown in FIG. 6C, or on the crown 46 without detracting from the invention. The notch area 58 can be formed in a variety of force focusing shapes, including but not limited to a partial pyramid shape, a V-shape, or a partial conical shape.

A cover 60 of the removable cap 44 is sealed over the sealed opening 42 by the frangible area 48. The cover 60 has a thickness sufficient to resist manual piercing by needle 18 or piercing pin 20. Due to the melt temperature of the material of the cover 60 being in the range of 129-144° C. and the presence of an air chamber under the cover once assembled, the cover 60 is adapted to shape changes during heat sterilization, which allows a user to discern the sterilized state of the additive port closure assembly 22 due to the shape of cover 60.

A pull element 62 of the removable cap 44 is connected to the cover 60 to allow a user to manually tug on the pull element 62 to sever the frangible area 48 and separate the cover 60 from the crown 46. The pull element 62 includes a lever 64 connected to one side of the cover and adjacent to the crown 46. The lever 64 is positioned adjacent the notch area 58 and focuses the user tugging force on the pull element 62 at the notch area 58. The lever 64 includes an area of narrowed cross section that defines a pull force concentrator. The pull force concentrator is adjacent the frangible area 48 and near the notch area 58. Preferably the pull force concentrator is defined by a transverse groove 65 having rounded side walls in the top of the lever 64, although other shapes, orientations and locations will not detract from the invention so long as the structure focuses or concentrates the user tugging force on the pull element at the notch area 58.

A pull tab 66 is connected to the lever 64 by a pull ring 68 and positioned opposite the lever 64 on the pull ring 68. The pull tab 66 provides an area for a user to manually grip and tug on the pull element 62.

At least one pivot element 70 is radially spaced from the frangible area 48 and circumferentially spaced from the lever 64 on the pull ring 68. More preferably, a pair of pivot elements is positioned so each pivot element is equally spaced about ninety degrees away from the lever 64. The pivot elements 70 contact the crown 46 and pivot to absorb any impact forces on the pull element 62 to prevent inadvertent damage to the frangible area 48. Additional pivot elements may be utilized as needed.

With reference to FIGS. 3A, 4, 5 and 7, a reseal element 72 of the removable cap 44 is positioned between the under shell 40 of the crown 46 and the interior face 28 of the reseal housing 24. The reseal element 72 has an annular shoulder 74 extending radially from a central core 76. The annular shoulder 74 splits the central core 76 into an upper core 78 having a raised surface 80 and a lower core 82.

Figure 7:
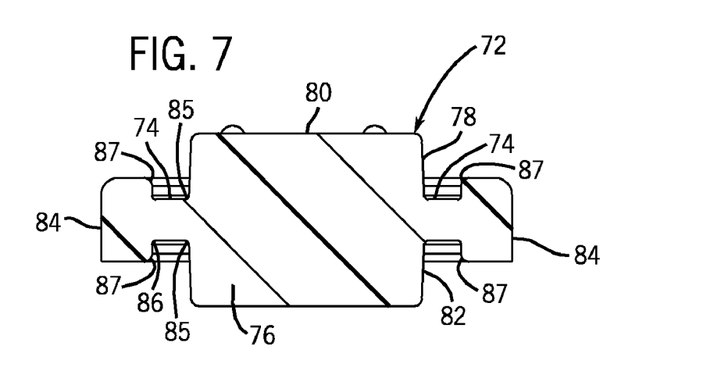
FIG. 7 is a sectional view of the reseal element of the present invention.

The raised surface 80 extends beyond the sealed opening 42 in the cap assembly 38 when the removable cap 44 is detached. The exposed raised surface 80 provides a convenient swabbable area to sterilize during subsequent uses.

The lower core 82 is received within the open cylinder 30 of the reseal housing 24. The diameter of the lower core 82 is selected relative to the diameter of the open cylinder 30 such that the open cylinder 30 presses radially inward on the lower core 82 to provide a seal therebetween and to re-seal the reseal element 72 itself when punctured. In other words, the lower core 82 is frictionally fitted or forcibly pressed into the open cylinder 30 of the reseal housing 24. This frictional fit provides one means of securing or retaining the reseal element 72 in the reseal housing 24 for subsequent assembly operations.

Figures 8, 9, 10:
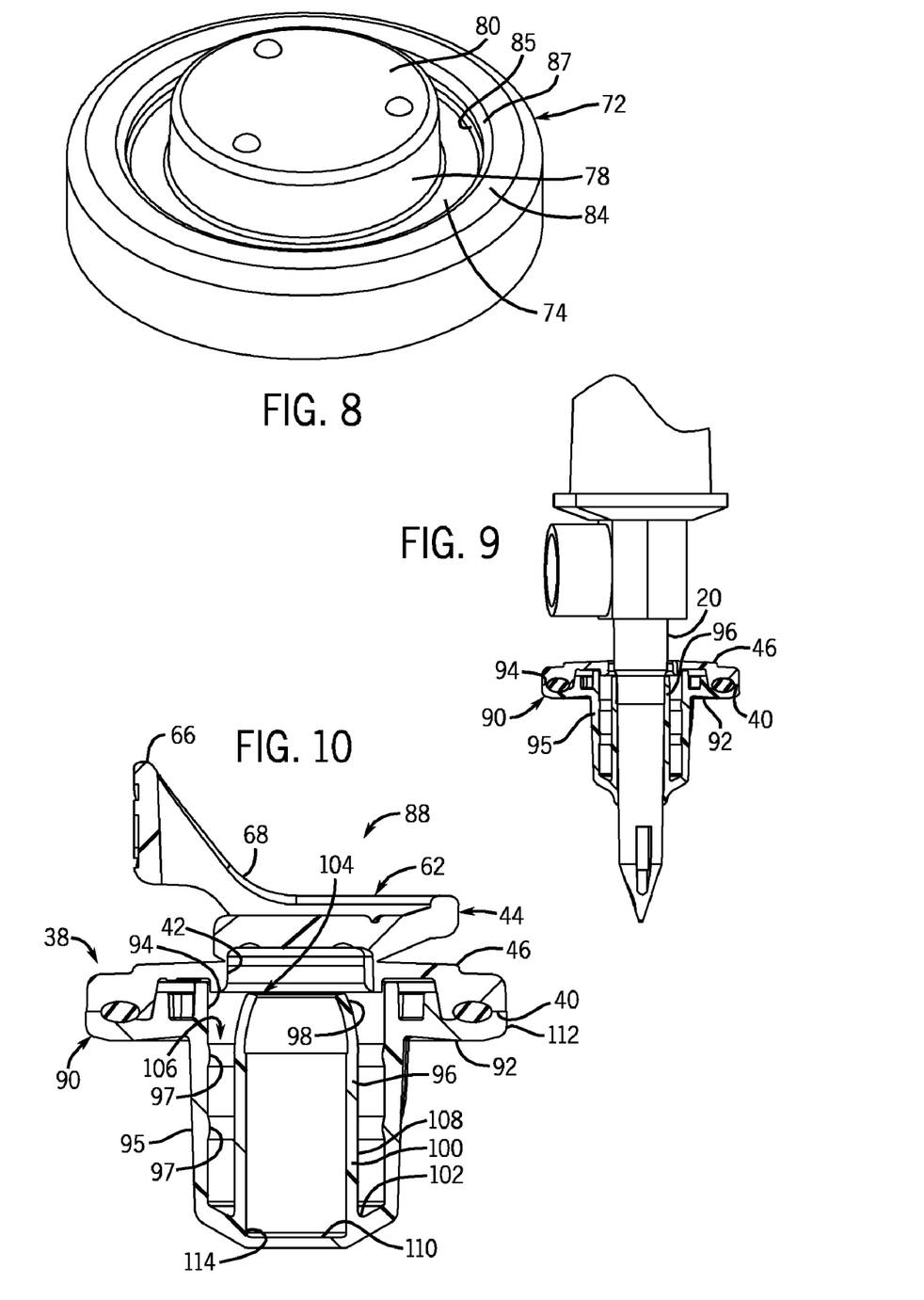
FIG. 8 is a perspective view of the reseal element of the present invention.
FIG. 9 is a sectional view of the administrative port closure assembly of the present invention in use with a piercing pin set.
FIG. 10 is a cross sectional view of one embodiment of the administrative port closure assembly of the present invention.

An annular lip element 84 is connected to an outer rim 86 of the annular shoulder 74. The junction of the rim 86 and the lip element 84 has a fillet or inside radius 85. The lip element 84 extends transversely to the annular shoulder 74 in two directions. The upper and lower inside edges of the lip element 84 have a chamfer, inside radius or fillet 87 thereon to assist in molding and guide the retaining rim 54 or rim 32 toward the annular shoulder 74. The annular lip element 84 has an inside diameter greater than the outside diameter of the retaining rim 54 and an outside diameter less than the outer diameter of the crown flange 56. The reseal element 72 is mechanically retained, held, secured, or more particularly clamped in place by the retaining rim 54 of the crown 46 and the upper rim 32 of the open cylinder 30, which upon the cap assembly 38 and reseal housing 24 being connected together are received between the central core 76 and the lip element 84 so as to retain the annular shoulder 74. The uncompressed height of the annular shoulder 74 can be selected to be equal to, or more preferably greater than, the distance between the retaining rim 54 and the rim 32 when the cap 44 and reseal housing 24 are joined. Selecting an uncompressed height greater than the available distance provides a desirable clamping force or sealing on the resilient material of the reseal element 72 at the shoulder 74. Alternatively, there may initially be a small gap between the retaining rim 54 and the upper surface of the shoulder 74. The gap may remain or be eliminated when, upon heat sterilization of the assembly 22, the cap 44 deforms. In the latter case, the rims 32, 54 abut or contact the lower surface and upper surface respectively of the annular shoulder 74. Thus, the crown 46 and the reseal housing 24, along with the annular shoulder 74 and the lip 84 of the reseal element, cooperate to provide a substantially permanent mechanical second means of securing the reseal element 72, which can be independent of the fit between the reseal element 72 and the open cylinder 30 and eliminates the need for separate fasteners, solvent bonding or swaging the reseal element 72 in place. In addition to positively retaining the reseal element 72 in place, the cap assembly 38 provides a removable cap 44 that seals the reseal element 72 from contamination until use. Despite the fact that the reseal element 72 is neither solvent bonded nor swaged into place, its securement is unaffected by component size, needle gauge, insertion force on the needle 18 or the removal of the cap 44. The reseal element 72 is automatically mechanically retained in place and constrained against movement both axially and radially primarily by the connection of the crown 46 and reseal housing 24.

With reference to FIGS. 1-3B, 9, and 10, an administrative port closure assembly 88 is shown as the second port closure assembly of the port closure system 10. The administrative port closure assembly 88 is adapted to provide piercing pin set 20 sterile access to the second fluid port 16. The administrative port closure assembly 88 is also adapted to be assembled and sterilized as a subassembly prior to association and use with the fluid container 12.

Figure 1:
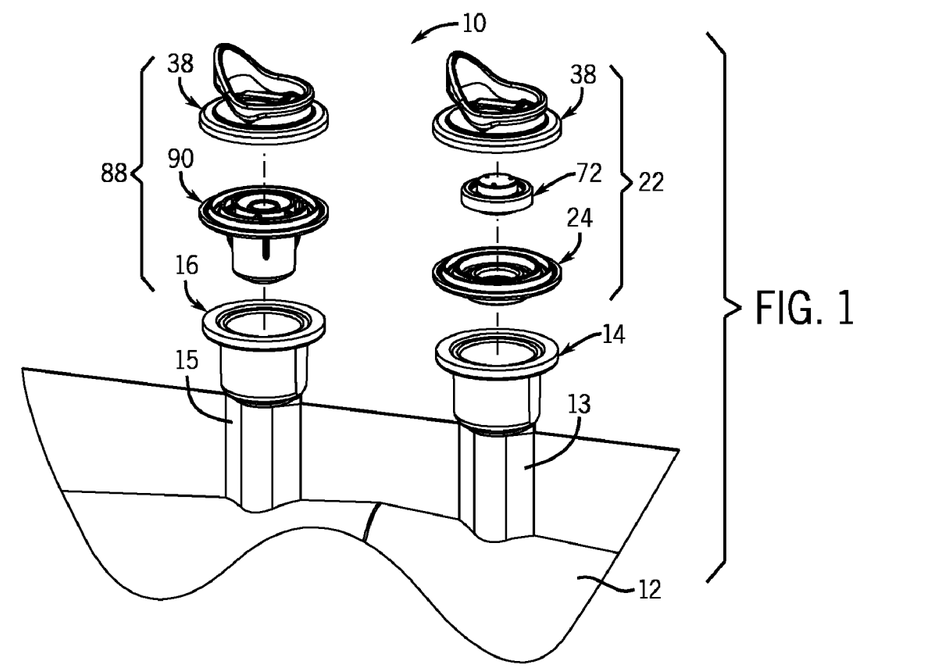
FIG. 1 is a partial exploded perspective view of the port closure system of the present invention in use with a fluid container.
Figure 2:
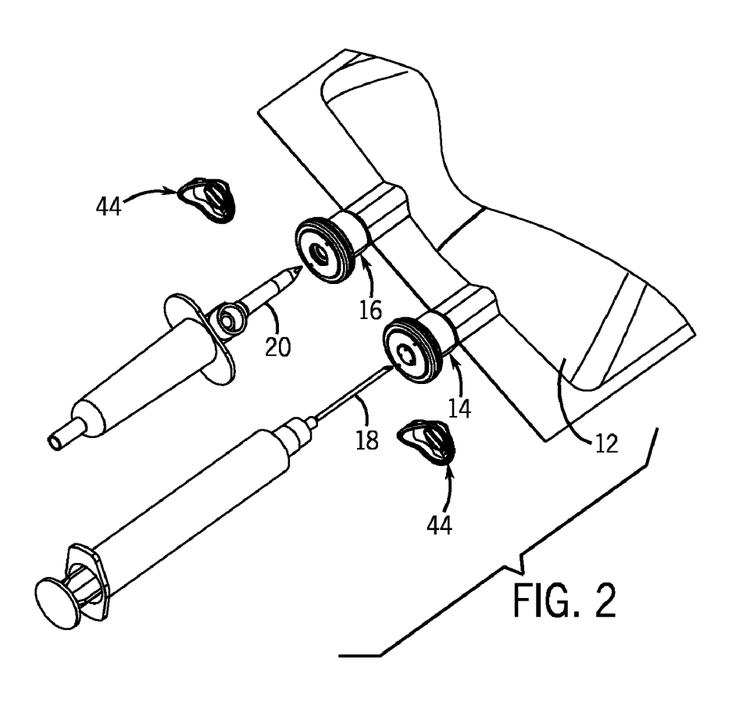
FIG. 2 is a partial perspective view of the port closure system of the present invention in use with a fluid container, needle and piercing pin set.
Figure 3A:
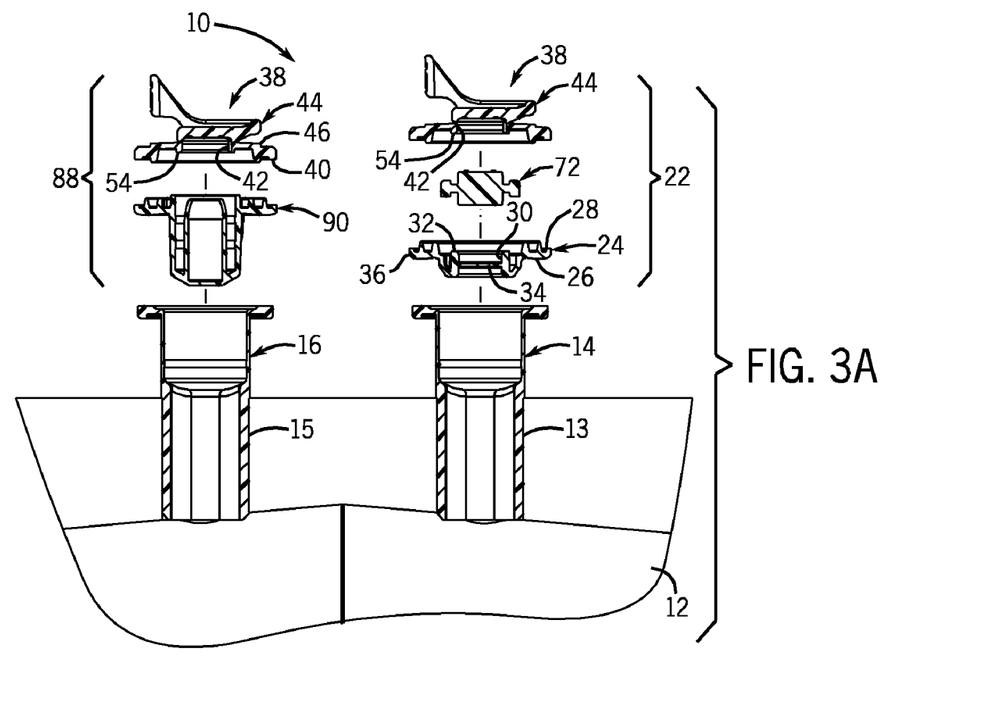
FIG. 3A is a partial sectional exploded view of the port closure system of the present invention in use with a fluid container.
Figure 3B:
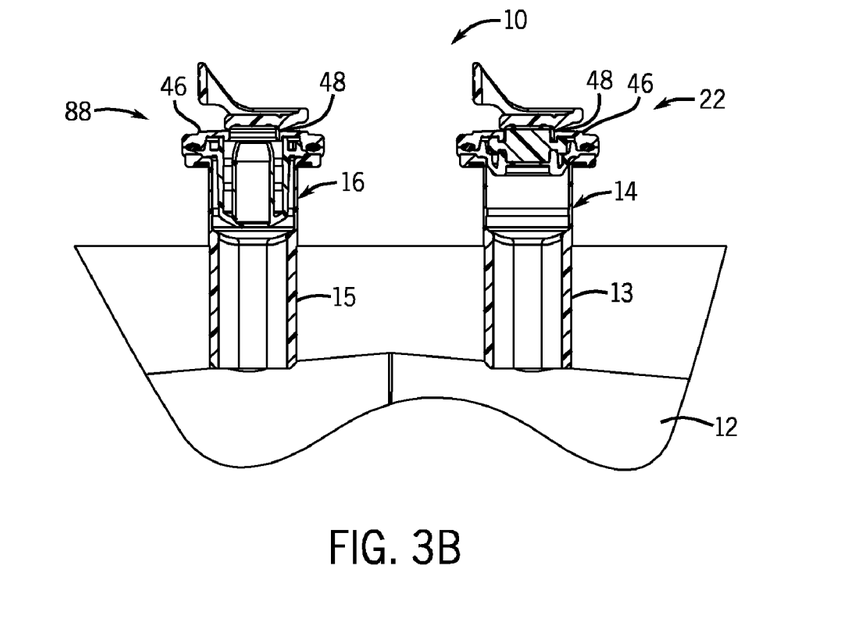
FIG. 3B is a partial sectional assembled view of the port closure system of the present invention in use with a fluid container.

With reference to FIGS. 1, 9 and 10, the administrative port closure assembly 88 includes a second port housing 90 (hereinafter "administrative housing 90") adapted to seal closed the second fluid port 16 by attachment to the fill tube 15. A base surface 92 is adapted to be associated with the second fluid port 16 or fill tube 15 and an interior surface 94 is adapted to face outwardly from the second fluid port 16.

A seal ring 95 extends from the base surface 92 and is adapted to be sealably received within the second fluid port 16. The seal ring 95 has a stiff construction and large diameter of about ⅝" to provide improved user handling of administrative port closure assembly 88. An optional stiffening hoop or rib 97, more preferably a pair of spaced ribs 97, extends radially inwardly on the seal ring 95 to stiffen the seal ring and resist deformation during heat sealing to the port 16 and later autoclave heat sterilization.

A sleeve 96 extends from the interior surface 94 past the base surface 92 and within the seal ring 95. The sleeve 96 is recessed below sealed opening 42 of second cap assembly 38 connected to the administrative housing 90. This recess protects the sleeve from inadvertent contamination of interior surface 94 when the administrative port closure assembly 88 is opened. The sleeve 96 has an upper portion 98 and a lower portion 100. The upper portion 98 is adjacent the interior surface 94 and has an opening 104 with a lesser diameter than the lower portion 100. The diameter difference between the upper and lower portions 98 and 100 allows the sleeve 96 to receive and sealably associate with differently sized piercing pin sets 20, and to accommodate diameter variation among various piercing pin sets 20.

In the embodiment disclosed in FIG. 10, the upper portion 98 has a substantially uniform wall thickness and is tapered inwardly into a bullet nose configuration where the exterior surface is convex and the interior surface is concave. The taper can be formed by any number of well-known manufacturing techniques, including but not limited to cutting, rolling (with or without heat) and swaging. The taper of the upper portion 98 is preferably curvilinear, but linear taper can also be used. During use the user's fingers are within ¼" of the sleeve 96, allowing the user to easily control the position of the sleeve 96 with respect to piercing pin sets 20.

The sleeve 96 and the seal ring 95 are connected at a flexible annular junction 102 at a base 114 for the sleeve to form a unitary body. The flexible junction 102 allows for some minor displacement of the sleeve 96 with respect to the rigid seal ring 95 during use.

An air-filled moat 106 is positioned between the seal ring 95 and the sleeve 96 on the base surface 92. The moat 106 allows the seal ring 95 to contract and expand as needed based on internal pressure of the container 12 during the heat sterilization cycle. Thus, the moat 106 protects the sleeve 96 from significant permanent deformation that could lead to leaks or unacceptable insertion or withdrawal force requirements. The connection between the seal ring 95 and sleeve 96 provides a clamping or sealing force on piercing pin set 20 (not shown) during pin insertion and withdrawal. In addition to being physically separated from the sealing ring 95 except at the base 114, the sleeve 96 is protected by the seal ring 95 and moat 106 from potential distortion during autoclaving, since the moat 106 reduces outside pressure against sleeve 96 during autoclaving.

An administrative diaphragm 110 is connected to the sleeve 96 to seal the sleeve 96 closed to fluid flow. The administrative diaphragm 110 is opened to fluid flow once pierced by piercing pin set 20.

An administrative flange 112 extends generally radially from the seal ring 95, and thus from the sleeve 96. The administrative flange 112 around the sleeve 96 creates an effective target area for the user to apply the piercing pin set 20 toward and protects the user from accidental pricks.

A second cap assembly 38 is connected to the administrative housing 90 to form the administrative port closure assembly 88. The under shell 40 is shaped to mate with the interior surface 94 of the administrative housing 90. Once mated, the cap assembly 38 seals the interior surface 94 from potential contamination. The removable cap 44 provides access to the sealed opening 42 and thus the interior surface 94. Once the removable cap 44 is detached, the administrative port closure assembly 88 need not be re-sterilized, as the cap assembly 38 operates as a sterile barrier to shield the interior surface 94 from potential contamination.

With reference to FIG. 1, during manufacture of the port system 10, port housings 24/90, cap assembly 38 and reseal element 72 are mold formed. The additive port closure assembly 22 is formed by positioning reseal element 72 between the cap assembly 38 to the port housing 24, and permanently connecting the cap assembly 38 to the port housing 24. The administrative port closure assembly 88 is formed by connecting the cap assembly 38 to the port housing 90. Port closure assemblies 22/88 are connected together by ultrasonically welding or radiant thermofusion welding the cap assembly 38 to the port housing 24/90. Port closure assemblies 22/88 are sterilized by irradiation. The irradiated pre-sterilized port closure assemblies 22/88 form subassemblies that are subsequently associated with or attached to the fluid container 12. The fluid container 12 is sealed to the irradiated port closure assemblies 22/88 by conventional means, including but not limited to ultrasonically welding, radiant thermofusion welding, or hot tongue heat sealing. The associated port closure assemblies 22/88 and fluid container 12 are then terminally heat sterilized by autoclaving after filling.

Port closure assemblies 22/88 are formed of a polymer blend that does not degrade during the irradiation, sterilization, radiant thermofusion welding, and ultrasonic welding. The term "degrade" as used herein refers to degradation to such an extent that the material is no longer suitable for its intended purpose. The polymer blend also provides ultrasonic sealability, radiant thermofusion sealability, and prevents coring when the polymer is punctured. The term "coring" as used herein refers to the process of a polymer fragmenting upon piercing so as to result in the formation of loose polymer particulate. The ability of polymer blend to be sealed by ultrasonic bonding and/or radiant thermofusion eliminates the need for any solvent or swaged bonding; and also eliminates the need to provide additional frictional force fit components to hold the port closure system 10 together. Additionally, the polymer blend provides a balance between insertion and withdrawal forces for improved handling by users.

One example of such a polymer blend includes but is not limited to a blend of 70% commercially available Atofina Z9470 and 30% commercially available Basell KS359P. Other suitable polypropylene copolymers and polyethylene copolymer blend could also be used without departing from the present invention.

Materials are selected for the IV fluid container 12, fill tube 13, 15, port housings 24, 90, and cap assembly 38 to provide, in conjunction with their design, the required container and port system functionality. While the difference in function among these parts requires different physical properties that may be supplied by a variety of materials, the materials must be compatible on a molecular level to enable them to be joined together without adhesives.

The fill tube 13, 15 is formed of a material that is sealable to the inner sealant surface of the IV fluid container 12 and the port housings 24, 90. It must be able to be autoclaved without deformation that significantly affects its appearance or function of providing a channel between the container 12 and the ports 14, 16. For sealant surfaces of containers 12 and port housings 24, 90 that comprise olefins such as polypropylene homopolymers, polypropylene copolymers, or blends of polypropylene copolymers with materials providing elastomeric properties, the fill tube 13, 15 preferably comprises a polypropylene homopolymer or copolymer. A homopolymer provides better dimensional stability through autoclaving, while a copolymer provides better compatibility with an IV container 12 that has a copolymer sealant surface. For container sealant surfaces and port housings that comprise random polypropylene copolymers or blends of random polypropylene copolymers with materials providing elastomeric properties, the fill tube 13, 15 preferably comprises a random polypropylene copolymer with ethylene content from about 2% to about 6% and a melting point from about 129° C. to about 145° C. To reduce deformation with autoclaving at 125° C., the random polypropylene copolymer more preferably has an ethylene content of about 2% and a melting point of about 145° C. Specifically, a random polypropylene copolymer, Atofina 7825, has been found to produce the best results at autoclave temperatures up to about 125° C. with a container 12 with polypropylene copolymer sealant layer and port housings 24, 90 comprising a blend of polypropylene copolymers.

The administrative port housing 90 must be heat sealable to both the fill tube 13 and cap assembly 38, as well as be stable to gamma radiation from 18-45 kGy, more preferably from 18-32 kGy. The administrative port housing 90 must be autoclavable up to about 125° C. without deformation that significantly affects its function of being able to accept and retain a piercing pin 20 with acceptable forces. Preferably the material selected for the administrative port housing 90 has a high melt temperature and good elastomeric properties. A material blend is preferred to provide properties not available from individual materials. A polypropylene based material is preferred primarily for its chemical compatibility with the polypropylene fill tube 13. Further material selection is dependent on radiation stability, autoclave temperature, and the range of piercing pin diameters to be used. Generally, polypropylenes with higher melting points such as homopolymers or copolymers with low ethylene content, for example Atofina 7825 that has 2% ethylene content, withstand autoclaving with less deformation. However, they have relatively high moduli, which increases piercing pin insertion force and limits the range of piercing pin diameters that may be used. They are also less stable to gamma radiation unless purposely stabilized with additives. While their performance may be improved by blending them with lower moduli, radiation stable olefins, it is preferable to use a high ethylene content (about 6% or greater) random copolymer as the base material. The high ethylene content improves radiation stability and lowers the modulus while maintaining acceptable resistance to autoclave deformation. It also reduces the concentration of the softening material required. Such softening material often has a lower melting point or is tacky and difficult to injection mold. Preferably a high ethylene content random polypropylene copolymer, such as Atofina Z9470, is used for the base material.

While an unmodified high ethylene content random polypropylene copolymer may provide acceptable performance with a single piercing pin diameter, it is preferable to soften the material with polyolefin copolymers such as thermoplastic polyolefin elastomers (TPEs) to broaden the range of acceptable piercing pin diameters and improve radiation stability. Acceptable performance also may be obtained with low ethylene content polypropylene random copolymer base materials with an appropriate selection of TPE and blend ratio. Similar to polypropylene copolymers, softer TPEs generally have lower melting points. Ethylene-hexene and ethylene-octene copolymer flexomers have very low moduli and melting points (72° C. and 55° C., respectively) substantially below the autoclave temperature of 125° C. However, when blended with a low ethylene content random copolymer at a ratio of 70% polypropylene copolymer/30% flexomer, they provide adequate softening and autoclave dimensional stability. An ethylene-octene flexomer, such as Dow Affinity EG8100, is preferred to reduce piercing pin insertion force. Polypropylene random copolymers with ethylene-propylene rubbers copolymerized in the copolymer matrix, such as Basell's Adflex materials, provide less softening than flexomers but have higher melt temperatures (approximately 144° C.). They are highly suitable for softening a high ethylene content random polypropylene copolymer base material, such as Atofina Z9470, because they reduce stiffness without reducing autoclave dimensional stability. Basell Adflex KS359P is one material that has been found to provide effective softening and radiation stability. Blends made from 40% Z9470/60% KS359P to 70% Z9470/30% KS359P may be used, with blends of about 70% Z9470/30% KS359P being more preferred.

The port cap assembly 38 must be sealable to both the administrative and additive port housings 90, 24 and stable to gamma radiation from 18-45 kGy, more preferably from 18-32 kGy. It must be autoclavable up to about 125° C. without deformation that significantly affects its function of maintaining sterility and being opened with an acceptable pull force. Key to an acceptable opening performance is developing an appropriate combination of material stiffness and tear detail thickness. The pull ring 68 or pull element 62 may snap off prior to opening the cap 44 with an excessively stiff material or thick tear detail. The pull ring 68 may stretch without opening the cap 44 or the cap 44 may deform during autoclaving with a material that is too soft. Materials that minimally provide the required properties are high ethylene content polypropylene copolymers such as Atofina Z9470 and random heterophasic polypropylenes such as Borealis Bosrsoft SD233CF. However, it is preferred to lower the opening force by using a TPE modifier. To maximize sealability to the administrative port housing 90, it also is preferred that the same materials be used in the same or similar ratio as used in the port housing 90. Basell Adflex KS359P again is highly suitable in that it provides softening without a loss in autoclave dimensional stability. A range of 100% Z9470/0% KS359P to 70% Z9470/30% KS359P is acceptable, with 70% Z9470/30% KS359P being more preferred.

Similar to the administrative port housing 90, the additive port housing 24 must be sealable to both the fill tube 13 and cap assembly 38 and stable to gamma radiation from 18-45 kGy, more preferably from 18-32 kGy. It must be autoclavable up to about 125° C. without deformation that significantly affects its function of being able to be pierced by a needle 18 without coring. To resist coring, it is preferred that the selected material has elastomeric properties. Polypropylene random copolymers with ethylene-propylene rubbers copolymers copolymerized in the copolymer matrix, such as Basell Adflex materials, are elastomeric and sealable to the 70% Z9470/30% KS359P port cap. Adflex KS359P is preferred among the Adflex materials for coring performance because it is the most elastomeric in the current Adflex product line. To improve seal strength by maximizing chemical compatibility and to improve ejection during injection molding, it is preferred to use the same materials in the same 70%/30% blend ratio as the cap assembly 38. To maximize coring performance at the intended port diaphragm 34 thickness of 18 mils, a range of 40% Z9470/60% KS359P to 0% Z9470/100% KS359P is preferred. To optimize injection molding, sealing, and coring performance, a 40% Z9470/60% KS359P blend is more preferred. The range may be adjusted depending upon diaphragm thickness, with thicker diaphragms generally requiring a higher elastomeric concentration. The blend of resins used for the various parts to be sonic or heat welded must provide melting points that are not so dissimilar as to prevent proper sealing security or reliability.

Figure 11:
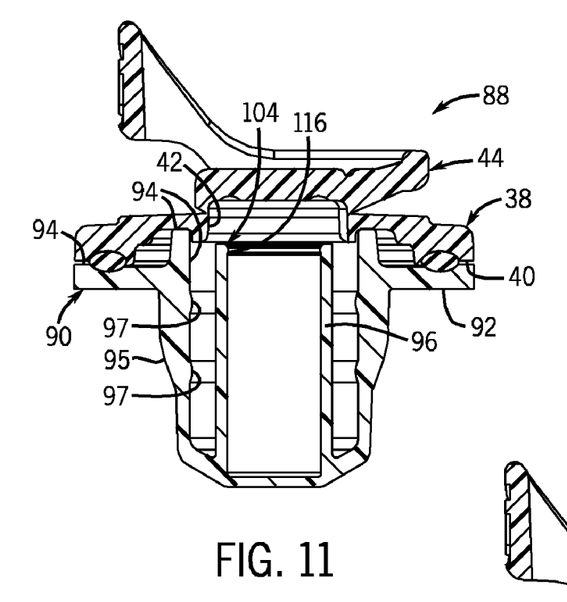
FIGS. 11-15 are cross sectional views of additional administrative port closure assembly embodiments.

With reference to FIG. 11, a still further embodiment of administrative port closure assembly 88 includes many of the same features as the embodiment of FIG. 10, but instead of the tapered sleeve end further includes a small wiper 116 adjacent the aperture 104 of sleeve 96 to seal against piercing pin set 20 (not shown). The sealing of the wiper 116 against the piercing pin set 20 (not shown) reduces the chance for fluid to leak out during activation. It will be understood to those skilled in the art that various methods including but not limited to swaging at the aperture 104 could be used to form the wiper 116. The wiper 116 could also be combined with a tapered sleeve end of FIG. 10.

Figure 12:
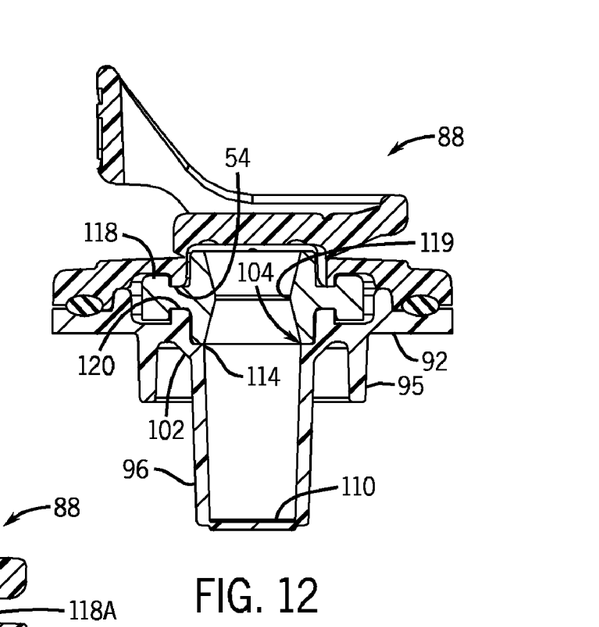

With reference to FIG. 12, a still further embodiment of administrative port closure assembly 88 includes some of the features of the embodiment of FIGS. 9-11 but further includes a pre-pierced administrative seal washer 118 having a wiping diameter 119, retained, secured, held, or more particularly (especially once heat sterilized) clamped in place between the retaining rim 54 and an administrative rim 120 extending from shoulder 102. The administrative seal washer 118 seals against piercing pin set 20 (not shown). To moderate and balance the forces required to insert and withdraw the pin set 20, the wiping diameter 119 can be centrally located and the pre-pierced diameter can be gradually increased as distance from the wiping diameter increases.

Figure 13:
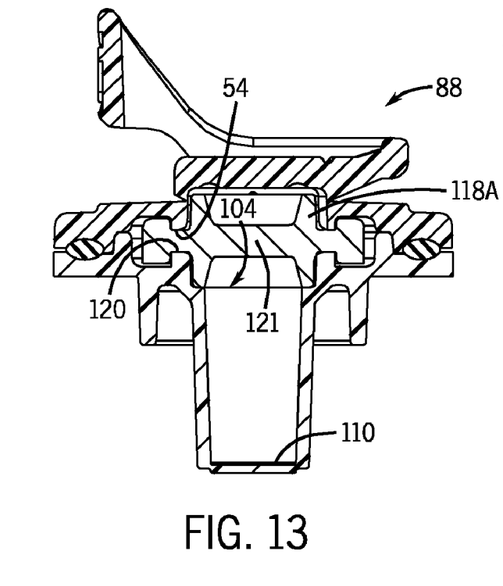

With reference to FIG. 13, a still further embodiment of administrative port closure assembly 88 includes some of the features of the embodiment of FIG. 12 but includes an administrative reseal 118A similar to the reseal element 72 of the additive port closure assembly 22, retained, secured, held, or more particularly clamped in place between the retaining rim 54 and an administrative rim 120 extending from shoulder 102. Similar to the reseal element in the additive port closure assembly 22, the administrative reseal 118A is clamped by the rims 54 and 120, especially once the assembly 88 is heat sterilized. The administrative reseal 118A seals against piercing pin set 20 (not shown). Since the reseal element 118A completely seals the opening 104 of the sleeve 96, the diaphragm 110 is optionally excludable in this embodiment. The central diaphragm 121 of the reseal 118A is relatively thick (greater than 0.050 inch or 1.27 mm) in the embodiment of FIG. 13. A still further embodiment can combine the features of FIGS. 12 and 13 so that the reseal element 118A includes a thin (0.010-0.050 inch or 0.254-1.27 mm) central diaphragm 121 rather than a pre-pierced opening or wiping diameter 119 or the thick central diaphragm 121 of at least 0.050 inch or 1.27 mm shown in FIG. 13. This thin diaphragm configuration is advantageous in that it makes the reseal element easier to mold and does not leave flash in undesirable areas.

Figure 14:
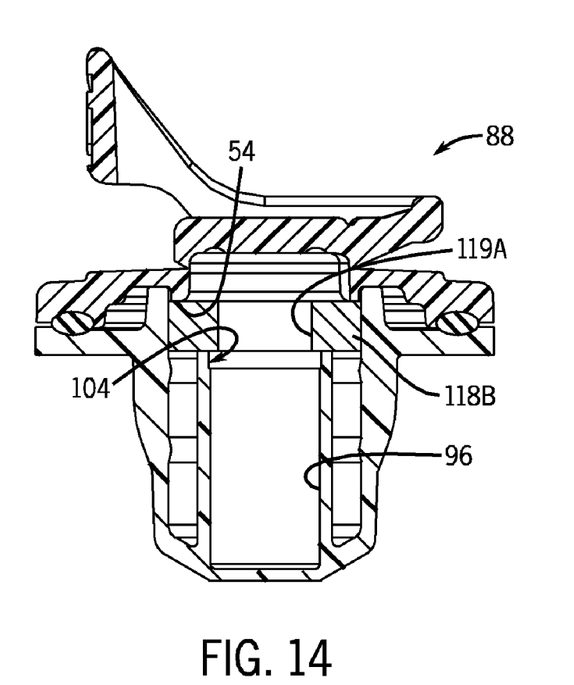

With reference to FIG. 14, a still further embodiment of administrative port closure assembly 88 includes some of the same features as the embodiment of FIG. 10, but further includes an either injection molded or extruded administrative sealing washer 118B with an inner diameter 119A that seals against piercing pin set 20 (not shown). The sealing washer 118B is retained, secured, held, or more particularly (especially once the assembly is heat sterilized) clamped in place between the retaining rim 54 and the sleeve 96.

Figure 15:
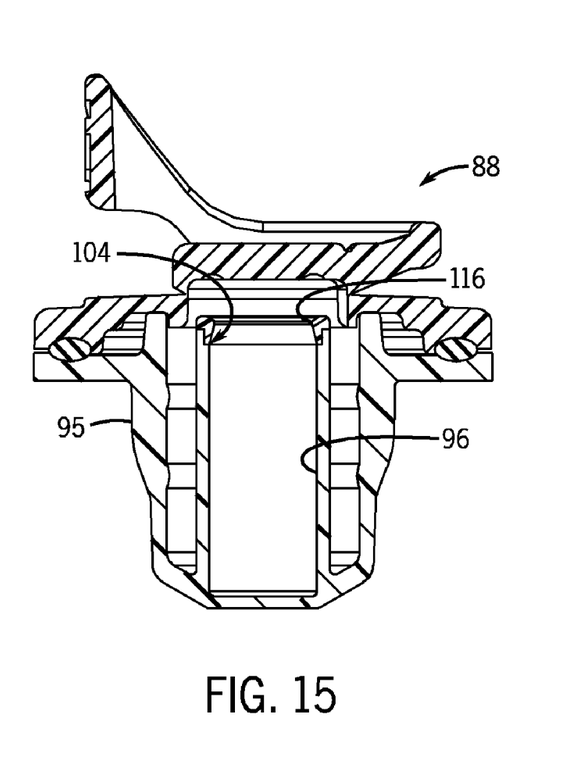

With reference to FIG. 15, a still further embodiment of administrative port closure assembly 88 includes a small wiper 116 similar to the embodiment of FIG. 11, but the wiper 116 and sleeve 96 form a unitary body that is molded through co-injection molding so that small wiper 116 has a different polymer content than sleeve 96. The wiper 116 is formed of isoprene and will generate holding forces during activation with the piercing pin set 20 (not shown).

Figure 16:
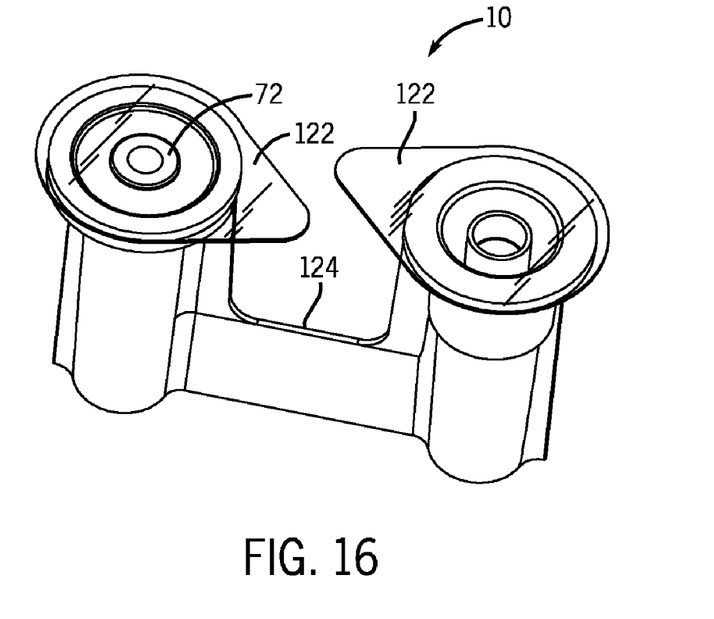
FIGS. 16-17 are perspective views of additional port closure system embodiments.

With reference to FIG. 16, another embodiment of port closure system 10 replaces cap assemblies 38 with cover foils 122. The cover foils 122 are made of pealable film stock. In this embodiment reseal element 72 is swaged in place. A body portion 124 joins the administrative port assembly 88 and additive port assembly 22.

Figure 17:
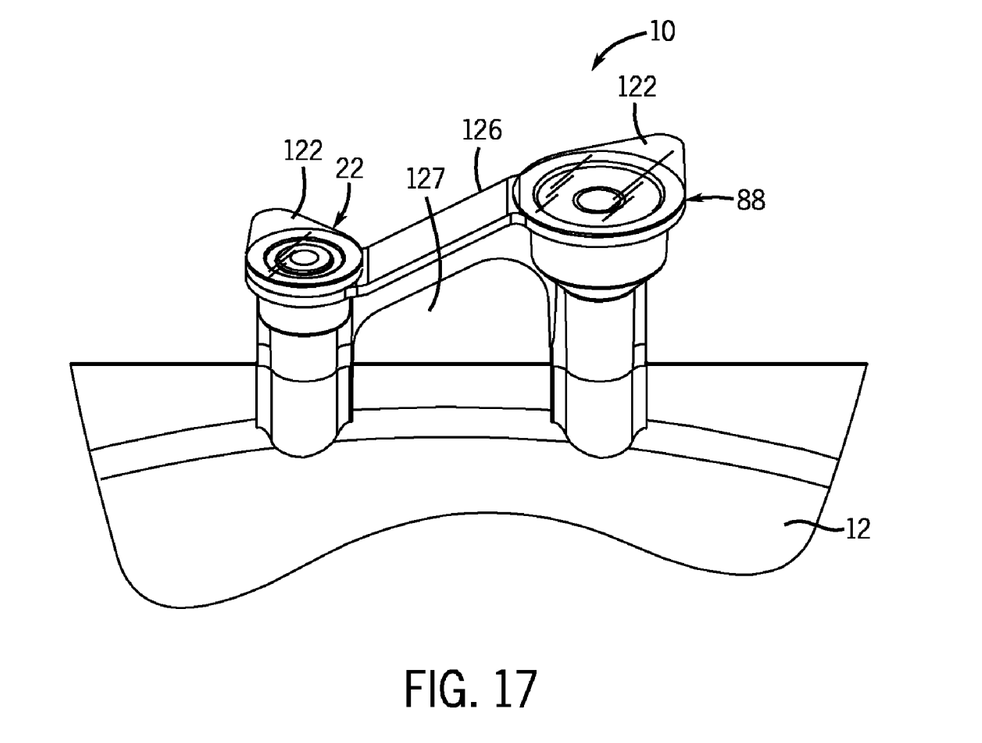

With reference to FIG. 17, a further embodiment of port closure system 10 includes the same features as the embodiment of FIG. 16, and further includes a handle element 126 joining the port assemblies 22, 88 so as to define a space 127 between the handle portion 126 and the fluid container 12, thus permitting a user to loop fingers around handle portion 126. Additionally, additive port assembly 22 is sized smaller than administrative port assembly 88 and is positioned lower with respect to the administrative port assembly 88, to further distinguish the additive port assembly 22 from the administrative port assembly 88.

Figure 18:
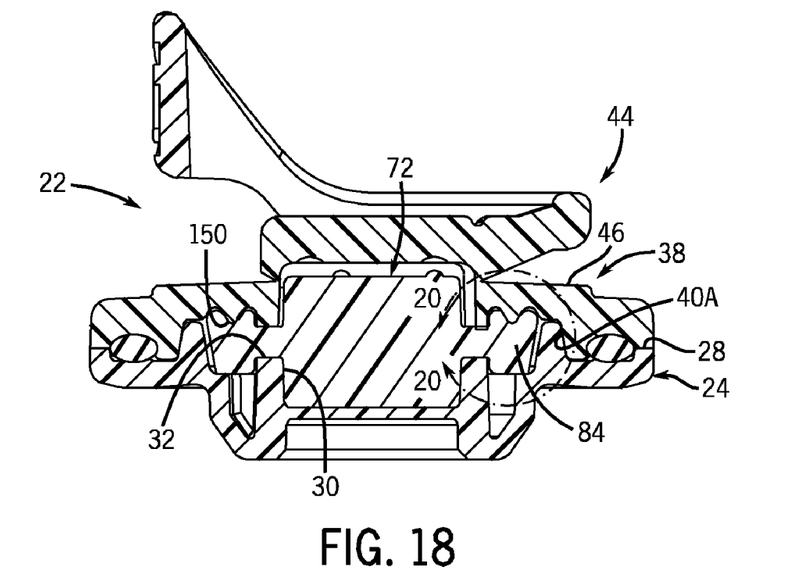
FIG. 18 is a cross sectional view similar to FIG. 4 of an alternative embodiment of the additive port closure assembly.
Figure 19:
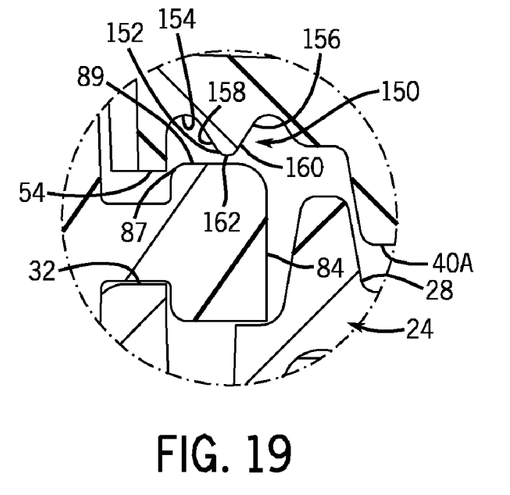
FIG. 19 is an enlarged partial cross sectional view of a portion of the additive port closure assembly from FIG. 18 prior to the cap assembly being joined to the reseal housing.
Figure 20:
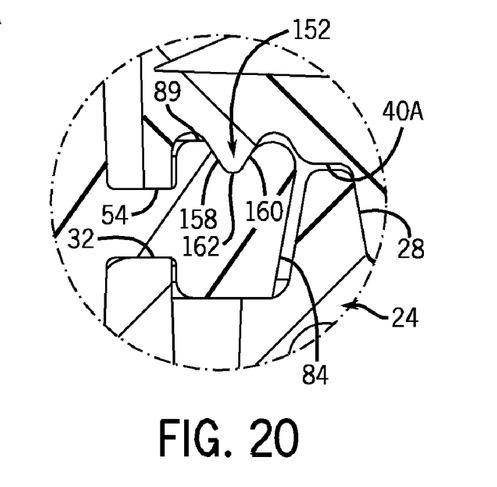
FIG. 20 is an enlarged partial cross sectional view of the additive port closure assembly and shows the area encircled by the line 20-20 in FIG. 18.

With reference to FIGS. 18-20, a further embodiment of the additive port closure assembly 22 includes a reseal housing 24 and reseal element 72 as described above. However, the under shell 40A of the cap assembly 38 differs in some respects from the under shell 40 previously described. The under shell 40A of the crown 46 includes at least one sealing element 150 for engaging the lip 84 of the reseal element 72. Preferably the sealing element 150 engages the top surface 89 of the lip 84.

Although one skilled in the art will appreciate from this disclosure that the sealing element 150 can take various forms and shapes, in the embodiment shown, the sealing element 150 includes at least one protrusion 152 that extends downwardly from the under shell 40A and defines troughs 154, 156 on either side thereof. The protrusion 152 can be generally V-shaped in cross section and have angled sides 158, 160 that converge to form a blunt, rounded tip 162. Preferably the protrusion 152 extends around the under shell 40A in a circular pattern. The circular pattern can be broken to form circumferentially spaced protrusions or can be unbroken to form a continuous annular protrusion. Alternatively, the sealing element 150 can include a plurality of concentrically arranged protrusions 152.

As best seen in FIG. 20, the sealing element 150 engages the lip 84 between the under shell 40A and the interior or inner surface 28 when the under shell 40A of the crown 46 is connected, attached or joined to the inner surface 28 of the reseal housing 24 as described above. The tip 162 and angled sides 158, 160 of the protrusion 152 or sealing element 150 contact and sealingly engage the top surface 89 of the lip 84. The reseal element 72 resiliently deforms around the protrusion 152. The engagement of the protrusion 152 with the resilient reseal element 72 provides a clamping force on the lip 84, clamping it between the protrusion 152 on the under shell 40A and the inner surface 28 of the reseal housing 24. When the sealing element 150 includes one or more protrusions 152 arranged a sufficiently closed annular pattern, this arrangement provides an effective seal against liquids, vapors and gases that might otherwise pass around the reseal element 72. The invention assists in preventing contamination from reaching the inner surface 28 when the user removes the detachable cap 44. Undesirable ingress and egress of liquids, vapors or gases is prevented during the sterilization of the port closure assembly 22 or the fluid container 12 to which the port closure assembly is attached. This embodiment of the invention provides the additional benefit of further restraining the reseal element 72 against movement that might otherwise occur during insertion or withdrawal of a needle 18 or similar piercing member.

One skilled in the art will appreciate that the principles of FIGS. 18-20 can be applied alone or in combination with other features disclosed herein. By way of example and not limitation, the principles are applicable to administrative port closure assemblies that utilize a reseal element, such as the embodiment of FIG. 13.

From the foregoing, it can be seen that the present invention accomplishes at least all of the stated objectives. The invention provides a port closure system that reduces the possibilities of contamination during storage and use, improves the ease of handling when fluids are to be withdrawn or introduced, and increases the ease and efficiency of manufacture.

We claim:

1. A reseal element for use with a fluid container having a fluid port of a given internal diameter, comprising:
   a central core adapted to provide resealable access to the fluid port, the central core having a cylindrical upper portion, a cylindrical lower portion having an outer diameter greater than the given internal diameter of the fluid port, and a cylindrical central portion interconnecting the upper portion and the lower portion;
   an annular shoulder directly attached to and extending radially outward from the cylindrical central portion of the central core;
   a lip element connected to the annular shoulder and extending transversely to the annular shoulder in two opposite, axial directions;
   the upper portion of the central core extending upwardly beyond the annular shoulder and the lip element and thereby defining a raised top surface of the reseal element;
   the lower portion of the central core extending downwardly beyond the annular shoulder and the lip element; and
   wherein the reseal element is adapted to be mechanically retained by clamping engagement of the annular shoulder along an annular path disposed between the central core and the lip element and substantially all of the lower portion of the central core has the outer diameter greater than the given internal diameter of the fluid port and is thereby adapted to be securely press fitted within the given internal diameter of the fluid port.

2. The reseal element of claim 1 wherein the annular shoulder has an outer rim and the lip element is connected to the outer rim of the annular shoulder.

3. The reseal element of claim 1 wherein the lower portion of the central core has a flat planar lower surface that spans across the outer diameter to define a full circular bottom surface area.

* * * * *